(12) United States Patent
Shen et al.

(10) Patent No.: US 8,389,698 B2
(45) Date of Patent: *Mar. 5, 2013

(54) TANAPROGET DERIVATIVES, METABOLITES, AND USES THEREOF

(75) Inventors: Li Shen, Audubon, PA (US); Kelly Keating, Champaign, IL (US); Oliver McConnell, Collegeville, PA (US); William DeMaio, Collegeville, PA (US); Appavu Chandrasekaran, Plainsboro, NJ (US)

(73) Assignee: Wyeth LLC, Madison, NJ (US)

( * ) Notice: Subject to any disclaimer, the term of this patent is extended or adjusted under 35 U.S.C. 154(b) by 543 days.

This patent is subject to a terminal disclaimer.

(21) Appl. No.: 12/492,229

(22) Filed: Jun. 26, 2009

(65) Prior Publication Data

US 2009/0306000 A1 Dec. 10, 2009

Related U.S. Application Data

(62) Division of application No. 11/201,696, filed on Aug. 11, 2005, now Pat. No. 7,569,679.

(60) Provisional application No. 60/601,254, filed on Aug. 13, 2004.

(51) Int. Cl.
C07H 17/00 (2006.01)
C07H 1/00 (2006.01)
C07H 1/06 (2006.01)
C07D 265/20 (2006.01)
C07D 413/04 (2006.01)
A61K 31/7042 (2006.01)
A61K 31/536 (2006.01)

(52) U.S. Cl. .......... 536/17.4; 536/18.6; 544/92; 544/96; 514/24; 514/43; 514/230.5

(58) Field of Classification Search .................. 536/17.4, 536/18.6; 544/92, 96; 514/24, 43, 230.5
See application file for complete search history.

(56) References Cited

U.S. PATENT DOCUMENTS

| | | | |
|---|---|---|---|
| 6,436,929 B1 | 8/2002 | Zhang et al. | |
| 6,455,572 B1 * | 9/2002 | Day et al. | 514/424 |
| 7,192,956 B2 | 3/2007 | Fensome et al. | |
| 7,268,149 B2 | 9/2007 | Fensome | |
| 7,446,211 B2 | 11/2008 | Wilk | |
| 7,569,679 B2 | 8/2009 | Shen et al. | |
| 2003/0092711 A1 | 5/2003 | Zhang | |

FOREIGN PATENT DOCUMENTS

| | | |
|---|---|---|
| JP | 2002/527454 | 8/2002 |
| JP | 2002/543192 | 12/2002 |
| JP | 2004/510693 | 4/2004 |
| WO | WO 9411030 A1 * | 5/1994 |
| WO | WO 00/22000 | 4/2000 |
| WO | WO 00/66570 | 11/2000 |
| WO | WO 01/77093 | 10/2001 |
| WO | WO-04/000230 | 12/2003 |
| WO | WO 04/000801 | 12/2003 |

OTHER PUBLICATIONS

Patani et al. Chem. Rev. 1996, 96, p. 3147-3176.*
Richter et al. Helv. Chim. Acta, 1975, 58(8), p. 2512-2517.*
Abolin et al. Science, 1980, 209, p. 703-704.*
Testa et al., Chem. & Biochem., 2008, 5, p. 2171-2336.*
Office Action issued in Australian Patent Application No. 2005272854 on Jan. 7, 2011.
Elmarakby, "Glucuronidation of Tanaproget, A Potent Non-Steroidal Progesterone Receptor Agonists, by Human UDP-Glucuronosyltransferases 1A9 and 2B7", AAPS J, 7(S2):W5266 (Abstract of presentation on Apr. 29, 2005).
Fensome, "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonist Tanaproget", J. Med. Chem., 48(16):5092-5095 (Jul. 12, 2005).
Han, "Targeted Prodrug Design to Optimize Drug Delivery", AAPS PharmSci, 2(1): Article 6:1-11 (Mar. 21, 2000).
Keating, "NMR Characterization of an S-Linked Glucuronide Metabolite of the Potent, Novel, Nonsteroidal Progesterone Agonists Tanaproget", Drug Metab. Disposition, 34(8):1283-1287 (Aug. 2006; e-pub: May 12, 2006).
Volin, "High-performance liquid chromatographic analysis of corticosteroids", J Chromatogr B Biomed Appl., 671(1-2):319-340 (Sep. 15, 1995).
Winneker, "Nonsteroidal progesterone receptor modulators: structure activity relationships", Semin Reprod Med., 23(1):46-57 (Feb. 2005).
Zhang, Novel 6-aryl-1,4-dihydrobenzo[d][ and ]oxazine-2-thiones as potent, selective, and orally active nonsteroidal progesterone receptor agonists, Bioorganic & Medicinal Chemistry Letters, 13(7):1313-1316 (Apr. 7, 2003).
Zhang et al., "Molecular and Pharmacological Properties of a Potent and Selective Novel Nonsteroidal Progesterone Receptor Agonist Tanaproget", J. Biol. Chem., 280(31):28468-28475 (Aug. 5, 2005; e-pub: Jun. 3, 2005).
Winneker, "A new generation of progesterone receptor modulators", Steroids, 73:689-701 (Aug. 2008; e-publication: Mar. 28, 2008).
Keijiro Takagi, "Yakabutsu-Gaku", Nanzando Co., Ltd., pp. 25-26, 1984.
Applicant's Response to the Office Action issued in related Australian Patent Application No. 2005272854 on Jan. 7, 2011.
Office Action dated Aug. 30, 2011 issued in related Japanese Patent Application No. 2007-525765.
Office Action dated Feb. 29, 2012 issued in related India Patent Application No. 1386/DELNP/2007.

* cited by examiner

*Primary Examiner* — Shaojia Anna Jiang
*Assistant Examiner* — Jonathan S Lau
(74) *Attorney, Agent, or Firm* — Howson & Howson LLP

(57) ABSTRACT

A method of generating synthetic metabolites of tanaproget derivatives thereof is provided. These compounds and methods of using these derivatives for detecting tanaproget metabolites in samples are provided.

6 Claims, No Drawings

TANAPROGET DERIVATIVES, METABOLITES, AND USES THEREOF

CROSS-REFERENCE TO RELATED APPLICATIONS

This application is a divisional of U.S. patent application Ser. No. 11/201,696, filed Aug. 11, 2005, which claims the benefit under 35 USC 119(e) of U.S. Patent Application No. 60/601,254, filed Aug. 13, 2004. These applications are hereby incorporated by reference.

BACKGROUND OF THE INVENTION

The present invention provides novel derivatives of tanaproget.

Tanaproget is a potent, non-steroidal progesterone receptor agonist being developed for use in contraception as an alternative to currently available oral contraceptives. The elimination of steroid progestins from contraceptive regimens may reduce the common side effects of oral contraceptives.

SUMMARY OF INVENTION

The present invention provides metabolites of the active compound tanaproget. These compounds are useful in methods and kits for monitoring therapy with tanaproget.

Among these metabolites, a rare S-linked glucuronide conjugate, S-glucuronide tanaproget has been isolated and now synthesized. Having first been identified as a metabolite, when a tanaproget glucuronide is delivered to a subject, it is a prodrug that is enzymatically cleaved to tanaproget by glucuronidase in vivo. Thus, the invention provides tanaproget glucuronide derivatives formulated for administration as a tanaproget prodrug. In one embodiment, administration is by the oral route to maximize the advantages of glucuronidase activity in the gut.

Other aspects and advantages of the invention will be apparent from the following detailed description of the invention.

DETAILED DESCRIPTION OF THE INVENTION

The derivatives of the invention are unique synthetic metabolites that are believed to be bioequivalent to the metabolites produced by a subject following administration of tanaproget. Thus, the derivatives of the invention are useful as standards in kits for monitoring tanaproget therapy, and for generating antibodies specific for tanaproget metabolites. Such antibodies are useful for monitoring and studying the effects of tanaproget therapy.

Further, the tanaproget glucuronide derivatives of the invention can be delivered to a subject as a pro-drug, which is cleaved to the active form of tanaproget in vivo. Thus, the invention further provides pharmaceutical compositions and kits containing the tanaproget glucuronide derivatives of the invention, and methods of using same to deliver tanaproget to a subject. A subject may include any mammal, preferably female, including humans and non-humans.

As used herein, the PR agonist compound termed "NSP-989" or "tanaproget" [Wyeth] is characterized by a core structure:

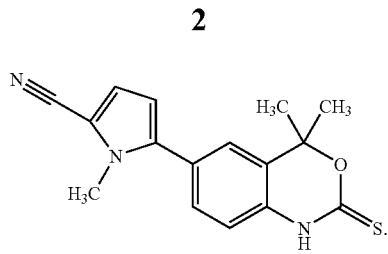

Methods for the synthesis of the illustrated core structure, 5-(4,4-dimethyl-2-thioxo-1,4-dihydro-2H-3,1-benzoxazin-6-yl)-1-methyl-1H-pyrrole-2-carbonitrile, are described in U.S. Pat. No. 6,436,929, U.S. patent application Ser. No. 11/113,794 (filed Apr. 25, 2005), and U.S. Provisional Patent Application Nos. 60/675,550 (filed Apr. 28, 2005); 60/675,551 (filed Apr. 28, 2005); 60/675,599 (filed Apr. 28, 2005); 60/675,737 (filed Apr. 28, 2005); and 60/675,738 (filed Apr. 28, 2005), as are uses for this compound. Other suitable synthetic methods for obtaining tanaproget will be readily apparent to one of skill in the art. The present invention is not limited by the means for producing tanaproget.

The present invention provides glucuronide derivatives of the above core structure. The derivatives of the invention may contain one or more asymmetric centers and may thus give rise to optical isomers and diastereoisomers. While shown without respect to stereochemistry below, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

In one embodiment, the glucuronide moiety is attached through the N atom in the oxindole ring. This derivative can be characterized by the structure:

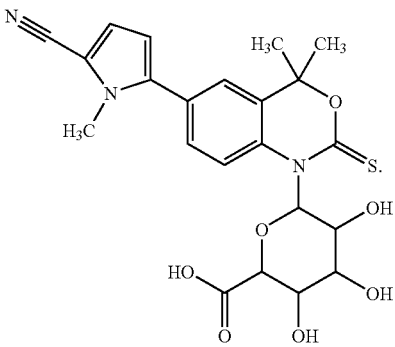 [SMILES: Cn1c(C#N)ccc1-c1ccc2c(c1)C(C)(C)OC(=S)N2C1OC(C(=O)O)C(O)C(O)C1O]

In another embodiment, the glucuronide moiety is attached through the S atom bound to the oxindole ring. In one embodiment, this derivative is characterized by the structure:

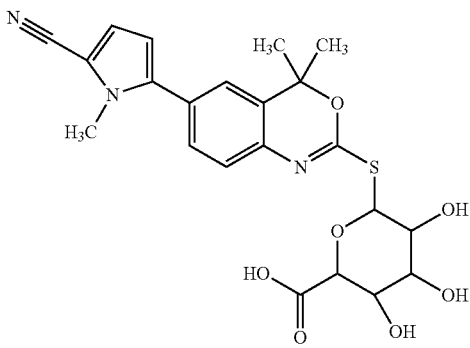 [SMILES: Cn1c(C#N)ccc1-c1ccc2c(c1)C(C)(C)OC(SC1OC(C(=O)O)C(O)C(O)C1O)=N2]

In other embodiments, these compounds have the following stereochemistry.

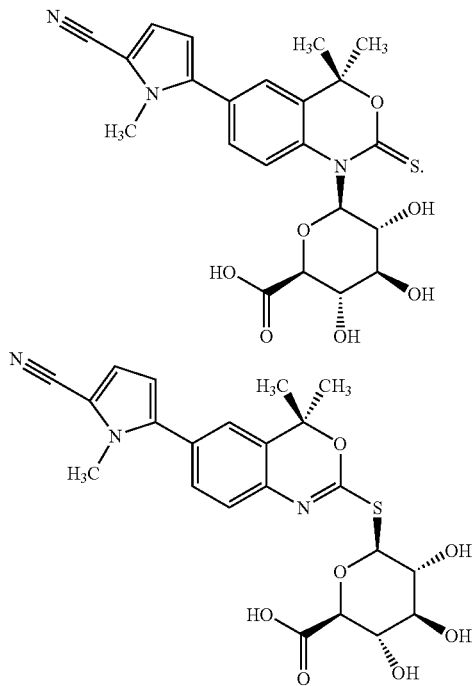

The tanaproget glucuronide derivatives of the invention may be produced synthetically, using conventional techniques. For example, a solution of tanaproget in anhydrous neutral solvent (e.g., DMF) is added dropwise under a nitrogen atmosphere to a solution of a strong base (e.g., sodium hydride) diluted in the solvent and then cooled using dry ice. After mixing, a solution of acetobromo-α-D-glucuronic acid ester is added.

The reaction solution is then warmed to room temperature, and stirred. After about 8 to 24 hours, the reaction solution is partitioned between water and an organic solvent, e.g., ethyl acetate. The aqueous layer is extracted. The combined organic layers are washed with saturated sodium chloride (NaCl) solution (100 mL), dried, and the solvent removed in vacuo.

Alternatively, the glucuronide derivates of the invention can be produced in an enzymatic system using suitable methods.

Conventional techniques can be used to recover the purified crude tanaproget derivatives. In one embodiment, the tanaproget derivatives may be purified by the means described in U.S. Provisional Patent Application No. 60/675,738 (filed Apr. 28, 2005), hereby incorporated by reference. In another embodiment, the crude extract can be passed through an HPLC reverse phase column with a gradient of solvents to remove unreacted tanaproget and the starting materials and reagents from the crude products. Suitable solvents for use in the gradients of a column can be readily selected by one of skill in the art. In the example herein, acetonitrile/methanol and acetonitrile/ammonium acetate were used as the solvents. The fractions, which contain tanaproget derivatives, are combined and the purified solvents are evaporated to provide the tanaproget derivative mixture. Thin layer chromatography or other chromatographic methods known in the art may be used for purification.

In order to isolate the individual derivatives, the purified mixture can be subjected to further separation using chromatographic techniques. For example, high performance liquid chromatography (HPLC) can be used. Suitable columns and conditions for separation will be readily apparent to one of skill in the art given the present disclosure.

In another aspect, this invention includes pharmaceutical compositions and treatments which comprise administering to a subject (e.g., a female of child bearing age for contraception or another mammal for therapeutic purposes) a pharmaceutically effective amount of one or more glucuronide derivatives of tanaproget as described above as agonists of the progesterone receptor.

The tanaproget glucuronide compounds of this invention, used alone or in combination, can be utilized in methods of contraception, pre-menopausal, peri-menopausal and/or post-menopausal hormone replacement therapy, and the treatment and/or prevention of skin disorders, dysfunctional bleeding, estrus synchronization, uterine leiomyomata, endometriosis, polycystic ovary syndrome, and carcinomas and adenocarcinomas of the endometrium, ovary, breast, colon, and prostate. Additional uses of the invention include stimulation of food intake.

The term "skin" is meant to describe the outer covering of a mammalian form including, without limitation, the epidermis, dermis, and subcutaneous tissues. Typically, the skin can include other components such as hair follicles and sweat glands. Skin disorders include, e.g., acne and hirsutism.

The term "acne" is meant to include any skin disorder where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa. The term "hirsutism" is meant to describe a skin disorder where an overgrowth of hair growth is observed in areas of the body which are not normally subject to excessive hair growth.

A number of skin disorders can be treated with the compounds of the present invention, including skin disorders of the hair follicles and sebaceous glands. In one embodiment, skin disorders such as acne and hirsutism, among others, can be treated according to the present invention.

Other skin disorders including dry/chapped skin, seboria, psoriasis, or alopecia can be treated using the compounds and compositions of the invention. The invention is also useful for treating the skin against the effects of environmental conditions.

This invention also includes pharmaceutical compositions utilizing the compounds herein, optionally in combination with a pharmaceutically acceptable carrier or excipient. When the compounds are employed for the above utilities, they may be combined with one or more pharmaceutically acceptable carriers or excipients, for example, solvents, diluents and the like, and may be administered orally in such forms as tablets, capsules, dispersible powders, granules, suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the tanaproget derivative in combination with the carrier, more usually between about 5% and 60% by weight.

The effective dosage of tanaproget derivative employed may vary depending on the particular tanaproget glucuronide derivative employed, the mode of administration and the severity of the condition being treated. However, in general, satisfactory results are obtained when the compounds of the invention are administered at a daily dosage of from about 0.5 to about 500 mg/kg of animal body weight, optionally given in divided doses one to four times a day, or in a sustained release form. For most large mammals, the total daily dosage is from about 1 to 100 mg, or from about 2 to 80 mg. Dosage forms suitable for internal use comprise from about 0.5 to 500 mg of the tanaproget derivative in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These tanaproget glucuronide derivatives may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the tanaproget derivative and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the tanaproget glucuronide derivatives is presently preferred.

These tanaproget derivatives may also be administered parenterally or intraperitoneally. Solutions or suspensions of these tanaproget derivatives as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The present invention provides kits or packages of pharmaceutical formulations designed for use in regimens described herein. In one embodiment, these kits are designed for daily oral delivery over 21-day, 28-day, 30-day, or 31-day cycles, among others, and for one oral delivery per day. When the compositions are to be delivered continuously, a package or kit can include the composition in each tablet. When the compositions are to be delivered with periodic discontinuation, a package or kit can include placebos on those days when the composition is not delivered.

In one embodiment, the kits are organized to indicate a single oral formulation or combination of oral formulations to be taken on each day of the cycle, including oral tablets to be taken on each of the days specified, and in a further embodiment, one oral tablet will contain each of the combined daily dosages indicated.

In one embodiment, a kit can include a single phase of a daily dosage of the compound of the invention over a 21-day, 28-day, 30-day, or 31-day cycle. Alternatively, a kit can include a single phase of a daily dosage of the compound of the invention over the first 21 days of a 28-day, 30-day, or 31-day cycle. A kit can also include a single phase of a daily dosage of the compound of the invention over the first 28 days of a 30-day or 31-day cycle.

In a further embodiment, a kit can include a single combined phase of a daily dosage of the compound of the invention and an estrogen over a 21-day, 28-day, 30-day, or 31-day cycle. Alternatively, a kit can include a single combined phase of a daily dosage of the compound of the invention and an estrogen over the first 21 days of a 28-day, 30-day, or 31-day cycle. A kit can also include a single combined phase of a daily dosage of the compound of the invention and an estrogen over the first 28 days of a 30-day or 31-day cycle.

In another embodiment, a 28-day kit can include a first phase of from 14 to 28 daily dosage units of the compound of the invention; a second phase of from 1 to 11 daily dosage units of an estrogen; and, optionally, a third phase of an orally and pharmaceutically acceptable placebo for the remaining days of the cycle.

In yet a further embodiment, a 28-day kit can include a first phase of from 14 to 21 daily dosage units of the compound of the invention; a second phase of from 1 to 111 daily dosage units of an estrogen; and, optionally, a third phase of an orally and pharmaceutically acceptable placebo for the remaining days of the cycle.

In another embodiment, a 28-day kit can include a first phase of from 18 to 21 daily dosage units of a compound of the invention; a second phase of from 1 to 7 daily dosage units of an estrogen; and, optionally, an orally and pharmaceutically acceptable placebo for each of the remaining 0 to 9 days in the 28-day cycle.

In another embodiment, a 28-day kit can include a first phase of 21 daily dosage units of a compound of the invention; a second phase of 3 daily dosage units for days 22 to 24 of an estrogen; and, optionally, a third phase of 4 daily dosage units of an orally and pharmaceutically acceptable placebo for each of days 25 to 28.

In still another embodiment, the daily dosage of each pharmaceutically active component of the regimen remains fixed in each particular phase in which it is delivered. It is further preferable that the daily dose units described are to be delivered in the order described, with the first phase followed in order by the second and third phases. To help facilitate compliance with each regimen, the kits may also contain the placebo described for the final days of the cycle.

A number of packages or kits are known in the art for the use in dispensing pharmaceutical agents for oral use. In one embodiment, the package has indicators for each day of the 28-day cycle, and may be a labeled blister package, dial dispenser package, or bottle.

Metabolites and Uses Thereof

The tanaproget glucuronide derivatives of the invention are useful for monitoring therapy with tanaproget or with a tanaproget prodrug (e.g., a S-glucuronide tanaproget compound) in a subject. Additionally, the invention provides other tanaproget metabolites useful for monitoring therapy with tanaproget and its prodrugs. When used as a reagent and/or a standard, the tanaproget metabolite compounds may be labeled, e.g., with a radioactive, fluorescent, or calorimetric tag.

In one embodiment, the invention further provides an isolated tanaproget metabolite, which can be enzymatically or synthetically produced. Such a metabolite can be selected from among a tanaproget glucuronide derivative. Other suitable metabolites contain the tanaproget core structure and optional substitutions, including, e.g., tanaproget having a sulfate moiety located on the thiocarbonyl group; tanaproget having a hydroxy group located on the pyrrole ring; tanaproget having a hydroxy group located on the phenylpyrrole ring; and tanaproget having a carbamate in place of the thiocarbonyl group.

One or more of these tanaproget metabolites can serve as a standard, i.e., for comparison purposes, in a method for detecting the presence of a tanaproget metabolite in a sample. A "sample" as used herein refers to a biological sample, such as, for example, tissue or fluid isolated from an individual (including without limitation plasma, serum, cerebrospinal fluid, urine, lymph, tears, saliva and tissue sections) or from in vitro cell culture constituents, as well as samples from the environment.

In another embodiment, one or more of the tanaproget metabolites can be used to generate an antibody or antibodies that are used to detect the presence of the tanaproget metabolites in a sample. Suitably, the antibody is a monoclonal or polyclonal antibody specific for a tanaproget derivative. In one desirable embodiment, such an antibody selectively binds to the tanaproget derivative of the invention, and distinguishes that metabolite from tanaproget and other metabolites thereof.

The term "antibody" as used herein is intended to include fragments thereof which are specifically reactive with tanaproget and/or its metabolites, e.g., an Fv fragment and a F(ab)$_2$ fragment.

An antibody specific to a tanaproget derivative of the invention can be prepared using standard techniques wherein the antigen is a derivative of the invention. See, e.g., Sambrook, Molecular Cloning: A Laboratory Manual, Cold Spring Harbor Press, Cold Spring Harbor, N.Y.

The polyclonal and monoclonal antibodies to specific sites of a tanaproget metabolite may be used for development of immunoassays or therapeutic drug monitoring (TDM) kits. Such assays could include, but are not limited to, direct, inhibition, competitive or sandwich immunoassays (ELISA or other assay systems), RIA, solid or liquid phase assays or automated assay systems.

Where a competitive assay is used, the competitor for the antibody may be a tanaproget derivative of the invention bound to the assay plate, or a labeled derivative, e.g., a fluorolabeled derivative, a radiolabeled derivative, or a tritiated derivative.

Where desired, a kit can be used to facilitate the methods of the invention. A kit of the invention may contain an appropriately labeled tracer, an antibody, standard, instructions for use, and packaging. The label for the tracer may be any suitable label, e.g., a radioactive, fluorescent or calorimetric label. Where convenient, the components of the kit may be in lyophilized form.

The assay procedure of the invention has the advantages that it may be carried out rapidly and simply using standard bioanalytical equipment to give accurate and reproducible results. Also, whole blood may be used without the need for extraction.

The invention also provides an assay kit suitable for detecting the amount of tanaproget metabolite in a sample (e.g., blood or urine). In one embodiment, the kit comprises a binding competitor that displaces the pharmaceutical from tanaproget metabolite in the sample; and an antibody that binds to the pharmaceutical but not significantly to the binding competitor.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

The following examples are illustrative of the methods for generating compounds of the invention.

EXAMPLE 1

Preparation of Tanaproget S-Glucuronide from Rat Liver Microsomes

The glucuronide of tanaproget was prepared in male rat liver microsomes, and the structure was identified as a S-glucuronide conjugate by liquid chromatography (LC)/mass spectrometry (MS) and nuclear magnetic resonance (NMR) spectroscopy. This metabolite was also identified as a major metabolite in both male and female rat, dog, and human liver microsomes, and it was also the major drug related component found in rat, dog, and human plasma. This S-glucuronide can also be synthetically prepared simultaneously with a N-glucuronide. The two synthetic glucuronides could be separated by HPLC and their structures were all characterized by LC/MS and NMR spectroscopy. In the following scheme, the NSP-989 terminology is used in the place of tanaproget.

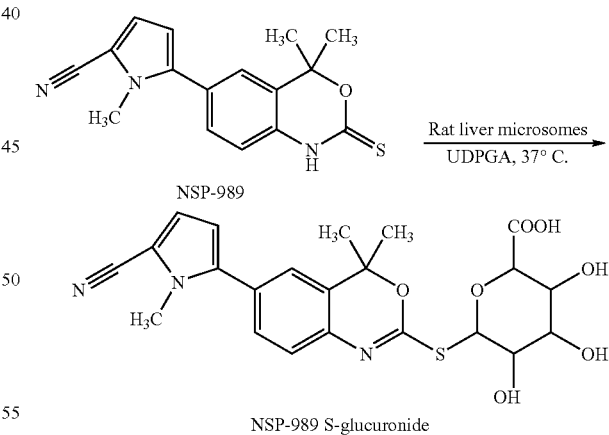

A. Incubation of Tanaproget and Extraction of Tanaproget Glucuronide

Liver microsomes from Sprague-Dawley rats were prepared in-house using a differential ultracentrifugation method described by Lake [Lake, B. In *Biochemical Toxicology: A Practical Approach*, Snell, K, Mullock, B (eds), IRL Press: England, 1987, 183-215] with slight modifications. Microsomal protein and cytochrome P450 content were determined by the method of Bradford [Bradford, MM *Anal. Biochem.* 1976; 72:248-254] and Omura and Sato [Omura, T, Sato, R *J. Biol. Chem.* 1964; 238:2370-2378], respectively. The protein concentration and P450 content were 50.9 mg/mL and 0.42 nmol/mg protein, respectively. Ammonium acetate, magnesium chloride, and uridine diphosphoglucuronic acid (UDPGA) were purchased from Sigma Chemical Company (St. Louis, Mo.). The solvents used for extraction and for chromatographic analysis were HPLC grade or ACS Reagent Grade (Mallinckrodt Baker, Phillipsburg, N.J.).

Incubations (100 mL) were performed with tanaproget (40 µM), UDPGA (5 mM), magnesium chloride (10 mM), and male rat liver microsomes (1.5 mg/mL), in 0.1 M potassium phosphate buffer, pH 7.4 at 37° C. The samples were pre-incubated for 1 minute at 37° C., and the reactions were initiated by the addition of UDPGA. The sample was cooled using an ice bath to stop the reaction after 3 hours. Unreacted tanaproget was removed from the samples by two extractions with diethyl ether (200 mL×2).

Tanaproget glucuronide and remaining unreacted tanaproget were extracted by solid phase extraction using C-18 cartridges and elution with methanol (10 mL). The methanol eluent was dried by rotary evaporation under vacuum at room temperature. The residues were extracted with 50% acetonitrile in water (5 mL) and centrifuged at 3500 rpm for 15 min. Aliquots (800 µL) of supernatants were analyzed by a Waters 2690® HPLC system with a semi-preparative column. Separation of the tanaproget metabolites was accomplished on a Phenomenex Luna™ column (C18, 250×10 mm ID, 5 µm particle size) (Phenomenex, Torrance, Calif.) and metabolites were detected by monitoring UV absorbance at 310 nm. The autosampler temperature was set to 6° C., while the column was at room temperature. Ammonium acetate (10 mM, pH 4.5) and acetonitrile were used as mobile phase A and B, respectively. The following gradient at a flow rate of 2 mL/min with a 5 min post run re-equilibration was employed: 0 min 20% B, 1 min 20% B, 10 min 40% B, 20 min 70% B, 25 min 95% B, 28 min 95% B, 30 min 20% B. Under these conditions, the tanaproget glucuronide peak (M1) at 15.5 min was collected for NMR spectroscopic analysis. Fractions containing the glucuronide conjugate peak were collected into clean tubes and frozen on dry ice immediately after collection. All glucuronide fractions were combined and acetonitrile was removed by rotary evaporation. The glucuronide was extracted from the aqueous eluates by solid phase extraction using C-18 cartridges. Water (2 mL) was used to wash residual buffer and 50% methanol in water was used to elute the glucuronide conjugate. The methanol/water eluates were dried by rotary evaporation under vacuum at room temperature. The remaining aqueous solutions were transferred to a 5 mL conical vial to remove water by lyophilization. Drying of the solid residue was continued overnight to remove additional moisture prior to NMR spectroscopic analysis.

B. HPLC/MS Analysis Conditions.

A Micromass Quattro Ultima™ triple quadrupole mass spectrometer (Waters Corp., Milford, Mass.) was used in this work. It was equipped with electrospray ionization (ESI) interface and operated in both the positive and negative ionization modes. Settings for the mass spectrometer were: ESI spray 2.5 KV, cone 50V, mass resolution 0.7 Da±0.2 Da width at half height, desolvation gas flow 900-1000 L/h, cone gas flow 50-80 L/h, source block temperature 80° C., desolvation gas temperature 250° C. LC/MS data were analyzed with Micromass MassLynx software (Waters Corp., versions 3.5 and 4.0).

Solvents used for chromatographic analysis of tanaproget glucuronide isolated from rat liver microsomes were HPLC grade or ACS Reagent Grade (Mallinkrodt Baker, Phillipsburg, N.J. and EMD Chemicals, Gibbstown, N.J.). The HPLC system in conjunction with the mass spectrometer was a Waters Alliance model 2695™ HPLC system. It was equipped with a built-in autosampler and a model 996 diode array UV detector set to monitor 210-350 nm. Separations were accomplished on a Phenomenex Luna C18(2) column (150×2 mm, 5 µm) (Phenomenex, Torrance, Calif.) with a Deltabond™ C18 guard column (10×2 mm) (ThermoElectron Corp., Bellefonte, Pa.). The flow rate was 0.3 mL/min. During LC/MS sample analysis, up to 10 min of the initial flow was diverted away from the mass spectrometer prior to evaluation of metabolites. Mobile phase A was 10 mM ammonium acetate in water, pH 4.5, (diluted from a 0.5 M stock solution of equal molar amounts of ammonium acetate and acetic acid) and mobile phase B was acetonitrile. The linear mobile phase gradient used was: 0 min 10% B, 1 min 10% B, 10 min 15% B, 35 min 17.5% B, 36 min 25% B, 50 min 30% B, 55 min 50% B, 60 min 90% B, 62 min 90% B, 65 min 10% B, 75 min 10% B.

C. LC/MS Results

Tanaproget glucuronide produced protonated and deprotonated molecular ions ([M+H]$^+$ and [M−H]$^−$, at m/z 474 and 472, respectively), which indicated a molecular weight of 473. This was 176 Da larger than tanaproget. Loss of 176 Da from m/z 474 in the positive ionization mass spectrum and from m/z 472 in the negative ionization mass spectrum generated the fragment ions at m/z 298 in the positive ionization mode and m/z 296 in the negative ionization mode, which are assigned as tanaproget. The glucuronic acid ion fragment was observed at m/z 175 in negative ionization mode. The m/z 339 fragment ion appears to be from fragmentation of the glucuronic acid ring. These data were consistent with glucuronic acid conjugation of tanaproget.

D. NMR Spectroscopy

Deuterated dimethylsulfoxide (DMSO-$d_6$) was used for all NMR samples.

For the metabolite samples isolated from rat liver microsomes, dissolution was done in a glove bag under argon to reduce absorption of atmospheric water. Typically 50 µL aliquots of a total of 200 µL of DMSO-$d_6$ were used to rinse the vial containing the vacuum dried sample and then transferred into a 3 mm NMR tube. NMR spectra were obtained at 500 (Varian Inova™ instrument), and 600 (Bruker Avance™ instrument) MHz. The bulk of the experimental NMR work was performed on the Varian Inova 500™ MHz instrument equipped with a Varian™ 3 mm $^1$H observe indirect detection probe. Chemical shifts δ (ppm) are reported relative to internal TMS (δ0.0) for $^1$H and $^{13}$C. In DMSO-$d_6$, $^1$H chemical shifts are referenced to residual protonated DMSO at δ2.49, and $^{13}$C chemical shifts are referenced to internal DMSO-$d_6$ at δ39.5. Chemical shifts for $^{15}$N are reported relative to liquid ammonia (δ0.0) and referenced to external formamide at δ112.0. Proton multiplicities are reported as s=singlet, d=doublet, dd=doublet of doublets, and m=multiplet. J values are given as $^1$H-$^1$H coupling constants in Hz.

General parameters for $^1$H-NMR experiments include a 5000 Hz spectral width, 32K data points, a 45° pulse width, a 1 second relaxation delay and the averaging of from 32 to >1000 scans, depending on sample concentration. Line broadening (~0.5 Hz) or gaussian processing routines were used to increase the signal-to-noise (S/N). General parameters for a $^{13}$C-NMR experiment include a 25,000 Hz spectral width, 64K data points, a 45° pulse width, a 1 second relaxation delay and averaging of at least 10,000 scans to achieve optimal S/N. In addition, 2 Hz line broadening was applied to increase S/N. All spectra were acquired at 25° C.

Several types of 2D NMR experiments were utilized to determine $^1$H—$^1$H and $^1$H—$^{13}$C connectivities. These included a gCOSY experiment for the determination of three-bond $^1$H—$^1$H connectivities, gHSQC and gHMBC experiments for the determination of one-, two-, three-, and four-bond $^1$H—$^{13}$C— connectivities, and a NOESY or ROESY experiment for the determination of through-space connectivities.

Despite several attempts at using freshly isolated tanaproget glucuronide samples, the purity and concentration of the samples were typically low (<70% pure and an estimated total amount of <20 μg in solution) which hampered acquisition of complete 2D NMR datasets. In addition, during the process of the microsomal incubation and subsequent isolation steps, the solution tended to rapidly produce the carbamate analog of tanaproget (the sulfur of tanaproget replaced by oxygen).

Nevertheless, sufficient chemical shift, coupling, and 2D NMR correlations were obtained to make nearly complete $^1$H and $^{13}$C assignments of tanaproget glucuronide isolated from rat liver microsomes. However, the location of the glucuronide attachment from the microsomally derived sample alone could not be determined. Only one key proton-carbon heteronuclear correlation was observed in the gHMBC NMR spectrum of the rat liver microsome incubation sample, that from H-1'(5.10 ppm) to C-6 (161.63 ppm). However, this same crosspeak was expected whether the metabolite was an N- or an S-glucuronide (i.e. 3-bond coupling in either case).

EXAMPLE 2

Preparation of Synthetic Tanaproget Glucuronide Conjugates

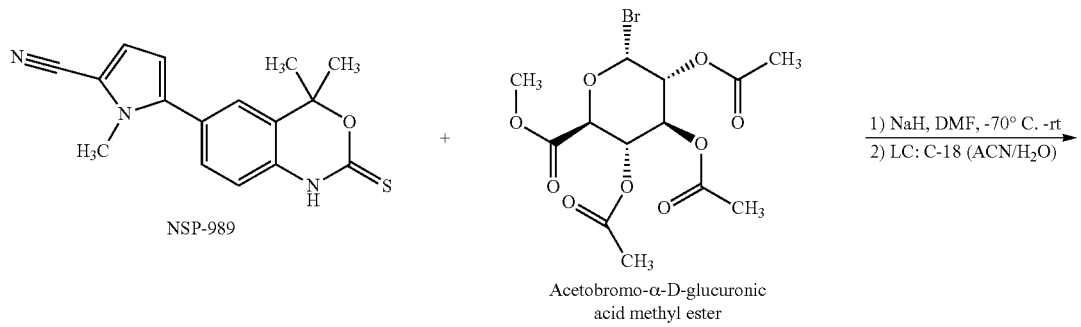

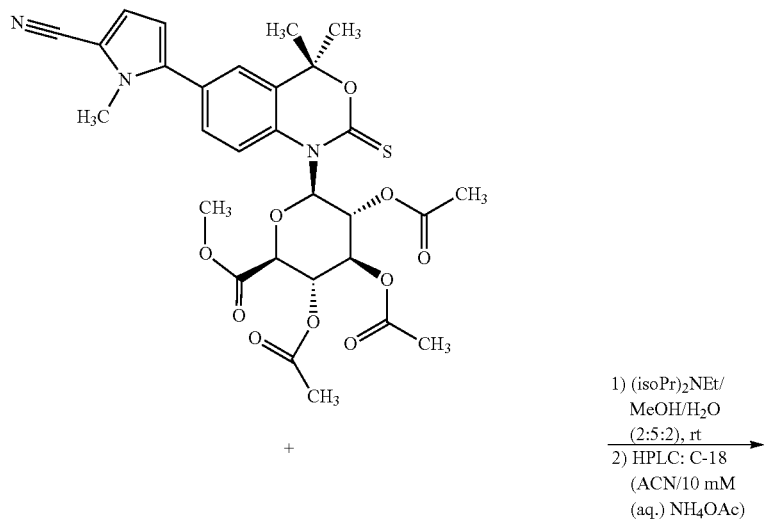

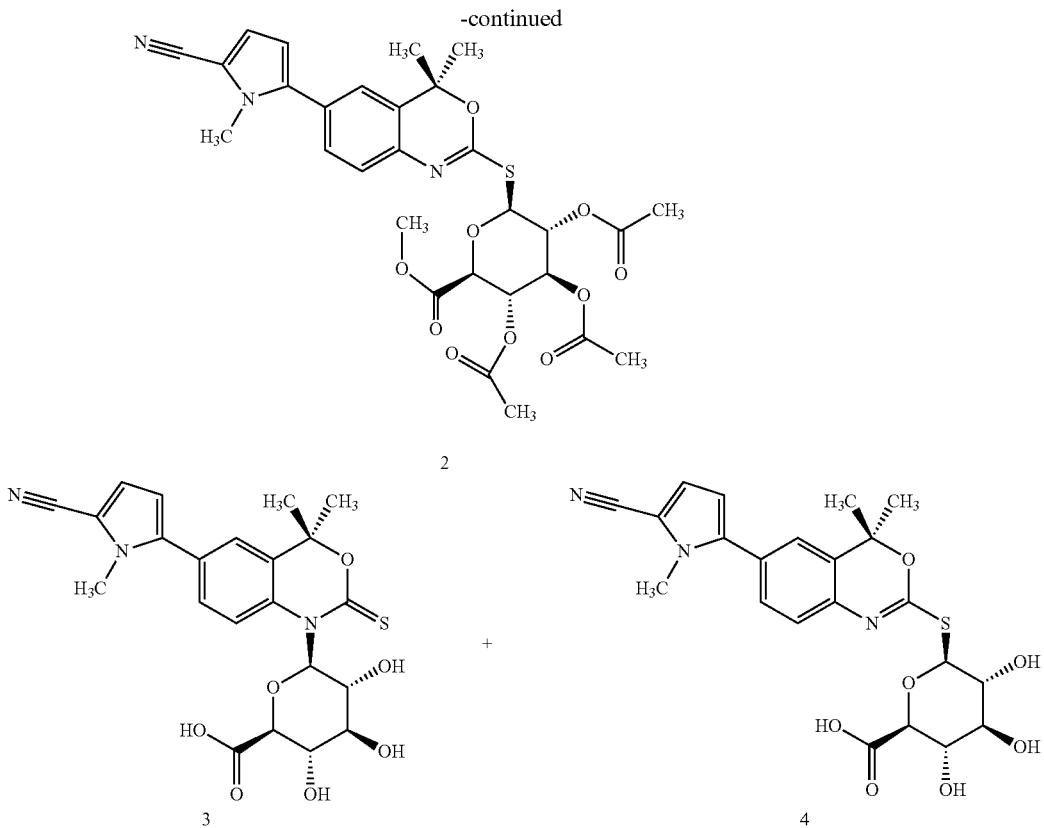

A. HPLC/MS and NMR Analysis Conditions:

HPLC/MS data for the synthetic compounds were acquired using a Waters Alliance 2695™ HPLC coupled to a Waters ZQ™ mass spectrometer. In general, the samples were analyzed using an open-access LC/MS method as previously described [Mallis, L M, Sarkahian, A B, Kulishoff, J M, Jr., Watts, WL, Jr. J. *Mass Spectrom.* 2002; 37:889-896].

Deuterated dimethylsulfoxide (DMSO-$d_6$) was used for all NMR samples except for 2, which was dissolved in $CDCl_3$ (deuterated solvents from Aldrich, Milwaukee, Wis.). NMR spectra were obtained at 300 (Bruker DPX™ instrument), 400 (Varian Inova™ instrument), 500 (Varian Inova™ instrument), and 600 (Bruker Avance™ instrument) MHz. The bulk of the experimental NMR work was performed on the Varian Inova 500™ MHz instrument equipped with a Varian™ 3 mm $^1$H observe indirect detection probe. Chemical shifts δ (ppm) in DMSO-$d_6$ are reported as described previously for tanaproget glucuronide. In $CDCl_3$, $^1$H chemical shifts are referenced to residual protonated $CHCl_3$ at δ7.27, and $^{13}$C chemical shifts are referenced to internal $CDCl_3$ at δ77.7. Chemical shifts for $^{15}$N are reported as described previously for tanaproget glucuronide.

General parameters for $^1$H-NMR and $^{13}$C-NMR experiments are as described previously for tanaproget glucuronide. All spectra were acquired at 25° C. 2D NMR experiments used to determine $^1$H-$^1$H and $^1$H-$^{13}$C connectivities were gCOSY, gHSQC, gHMBC, NOESY and ROESY.

B. Preparation of the Protected S-Glucuronide Acid (2) of Tanaproget

A solution of tanaproget (0.292 g, 1.0 mmol) in anhydrous dimethyl formamide (DMF) (10 mL) was added dropwise under a nitrogen atmosphere to a solution of sodium hydride (NaH) (0.052 g, 2.2 mmol) in DMF (50 mL) that was cooled to approximately −70° C. (dry ice). After stirring for 10 min, a solution of acetobromo-α-D-Glucuronic acid methyl ester (0.396 g, 1 mmol) in DMF (10 mL) was added dropwise. The reaction solution was then warmed to room temperature, and stirred for a total of 24 hours. After 24 hours, the reaction solution was partitioned between water (100 mL) and ethyl acetate (100 mL). The aqueous layer was extracted again with ethyl acetate (100 mL). The combined organic layers were washed with saturated sodium chloride (NaCl) solution (100 mL), dried (magnesium sulfate, $MgSO_4$), and the solvent removed in vacuo. Aliquots of the crude material were chromatographed under low-pressure reversed-phase C18 (RediSep/ISCO, 125×25 mm ID, 40 μm particle size) conditions with a gradient of 50-95% acetonitrile/water. Fractions eluting with 75-80% acetonitrile/water contained the S-protected (D)-Glucuronic acid derivative (2) of tanaproget. A total of approximately 200 mg of (2) was obtained at 95% purity based on NMR spectroscopic analysis (32% isolated yield). All chemicals were purchased from Aldrich (Milwaukee, Wis.) and used without further purification or drying.

C. Preparation of N-(3) and S-Glucuronic Acid (4) Derivatives of Tanaproget

In a separate reaction, a solution of tanaproget (0.146 g, 0.5 mmol) in anhydrous DMF (5 mL) was added dropwise under a nitrogen atmosphere to a solution of NaH (0.027 g, 1.1 mmol) in DMF (25 mL) that was cooled to approximately −70° C. (dry ice). After stirring for 10 min, a solution of acetobromo-α-D-glucuronic acid methyl ester (0.198 g, 0.5 mmol) in DMF (5 mL) was then added dropwise. The reaction solution was then warmed to room temperature, and stirred for a total of 8 hours. The reaction solution was partitioned between water (100 mL) and ethyl acetate (100 mL). The aqueous layer was extracted again with ethyl acetate (100 mL). The combined organic layers were washed with saturated NaCl solution (100 mL), dried (MgSO$_4$), and solvent removed in vacuo to yield 0.350 g of crude reaction material. To a portion of this material (0.210 g) was added a solution of MeOH/Hunig's base ((iso-Pr)$_2$NEt)/H$_2$O (5 mL/2 mL/2 mL) and the solution was stirred for 8.5 hours at room temperature. The pH of the reaction solution was then adjusted to 2.5 using HCl (concentrated, approximately 1.5 mL) and chromatographed by semi-preparative reversed-phase HPLC using YMC-Pack CN 150×20 mm, S-5 µm column with a gradient of 15-35% acetonitrile in 10 mM (aqueous) ammonium acetate. From repeated injections, approximately 5 mg of the N-(D)-glucuronic acid derivative (3) (3% isolated yield from tanaproget) and 15 mg of the S-(D)-glucuronic acid derivative (4) (10% isolated yield from tanaproget) was purified to >98% purity for NMR analysis and LC/MS analysis and comparison.

EXAMPLE 3

Comparison of Synthetic Compounds to M1

From extensive comparison of the spectral and chromatographic data of the microsomally-derived metabolite and the synthetic compounds, the metabolite has been determined to be the S-($\beta$)-D-glucuronide of tanaproget.

The positive ionization mode LC/MS spectrum (not shown) of synthetic compound 2, the protected S-glucuronide of tanaproget, gave a protonated molecular ion [M+H]$^+$ at 614, indicating a molecular weight of 613. Loss of 297 Da gave m/z 317, which is assigned to [M+H-tanaproget]$^+$. An ion signal at m/z 257 is assigned to m/z 317-acetic acid (C$_2$H$_4$O$_2$), and an observed ion at m/z 197 is assigned to m/z 257-acetic acid (C$_2$H$_4$O$_2$). Also, an ion at m/z 155 is assigned to m/z 197—acetyl (C$_2$H$_3$O)+H. The protonated and deprotonated LC/MS spectra (not shown) of the S-glucuronide 4 gave an [M+H]$^+$ ion at 474 and an [M−H]$^-$ ion at m/z 472, respectively, (as was also the case for 3, spectra not shown), indicating glucuronidation of tanaproget. Also observed for 4 in the positive and negative ionization mode mass spectra are the ions m/z 298 and m/z 296, assigned as tanaproget, that is, the loss of glucuronic acid. In addition, a fragment at m/z 175, assigned as glucuronic acid, was also detected in the negative ionization spectrum.

HPLC comparisons were also made to confirm whether the major synthetic glucuronide of tanaproget, S-glucuronide 4, was identical to tanaproget glucuronide, now proposed to be the S-glucuronide from the NMR and mass spectral results described above. Five different types of reverse phase HPLC columns were used under two different mobile phase conditions. These ten HPLC conditions covered a wide range of selectivity as evidenced by the change of elution order of the major and minor components in the samples. To compare and match the retention time of the major peaks in the two samples, spiking experiments were performed. The synthetic glucuronide that was determined to be S-glucuronide 4 was found to have identical retention times as the tanaproget glucuronide metabolite under all ten HPLC conditions.

Key NMR correlations in the synthetic compounds 3 and 4 which located the site of glucuronidation in tanaproget are described below. The proton chemical shift and coupling constant for the anomeric proton (H-1') with $\beta$-stereochemistry on the N-glucuronide is 6.31 ppm, and is a doublet with a coupling constant of 9.5 Hz. The carbon chemical shift of the anomeric carbon (C-1') is 90.2 ppm. The carbon chemical shift of the benzoxazine-2-thione carbon (C-6) of the N-glucuronidated metabolite of tanaproget is 188.0 ppm; this compared with the thiocarbonyl carbon of the benzoxazine-2-thione group observed in the parent molecule, tanaproget, at 182.8 ppm.

There are four important 3-bond correlations observed in the HMBC spectrum (not shown) of this molecule. They are from the anomeric proton (H-1') to the benzoxazine-2-thione carbon (C-6) and to the Sp2 aromatic carbon at 131.5 ppm (C-4), and from the protons H-7 and H-9, observed at 7.50 ppm and 7.57 ppm, respectively, to C-4. The proton chemical shift of the proton (H-10) that is in a position peri- to the N-glucuronide has moved downfield to 7.80 ppm, compared to 7.13 ppm in the parent molecule, indicating the proximity of the glucuronic acid group (and possibly the carboxylic acid moiety) to this proton. $^1$H-$^{15}$N gHMBC experiments were run on all compounds studied, but signals from the key nitrogen N-5 were not observed for any compound except tanaproget ($\delta$144.81), which had an HMBC crosspeak to H-10. The other nitrogen expected, N-15, was only observed in tanaproget ($\delta$154.99) and in 3 ($\delta$155.40), and in each compound had gHMBC correlations to H-17, H-18, and H-19.

The proton chemical shift and coupling constant for the anomeric proton (H-1') with $\beta$-stereochemistry on the synthetic S-glucuronide 4 is 5.11 ppm, and is a doublet with a coupling constant of 10.2 Hz. The carbon chemical shift of the anomeric carbon (C-1') is 85.0 ppm. The carbon chemical shift of the derivatized benzoxazine-2-thione carbon (C-6) of this S-glucuronidated metabolite of tanaproget is observed at 161.3 ppm, quite upfield shifted from the observed thiocarbonyl carbon chemical shift (182.8 ppm) of the benzoxazine-2-thione group observed in the parent molecule, tanaproget. There is a 3-bond correlation observed in the HMBC spectrum of this molecule between the anomeric proton (H-1') of the $\beta$-glucuronic acid and the derivatized benzoxazine-2-thione carbon (C-6). Finally, there is a 2-bond correlation observed in the HMBC spectrum between the gem-dimethyl protons (H-11 and H-12) observed at 1.59 ppm and 1.70 ppm and the carbon (C-2) to which this group is attached, observed at 81.5 ppm. These data confirm that the benzoxazine-2-thione (N(C=S)O) group of tanaproget did not rearrange to a thiolcarbamate (N(C=O)S) group before S-glucuronidation.

Comparison of the $^1$H NMR spectra and the NMR data derived from tanaproget glucuronide and the two synthetic compounds 3 and 4, revealed that tanaproget glucuronide must be the S-glucuronide derivative of tanaproget. The H1' chemical shift for tanaproget glucuronide is 5.10 ppm, and 5.11 ppm for 4, compared to H-1' at 6.31 ppm observed for 3. Also, C-6, in the benzoxazine-2-thione part of tanaproget, resonates at ~161 ppm for both tanaproget glucuronide and 4, but at 188.0 ppm for 3 and at 182.8 ppm for tanaproget.

EXAMPLE 4

Enzymatic Hydrolysis of Tanaproget Glucuronide conjugate Metabolite

In order to confirm that that the tanaproget glucuronide derivative is a prodrug when delivered to patients, the ability of the glucuronide conjugate to be enzymatically cleaved by a glucuronidase which is native to the gastrointestinal tract in humans was used in the following assay.

Pooled urine samples (4-8 hr) from healthy women were hydrolyzed by Glusulase®. Aliquots (1 mL) of pooled urine were adjusted to pH 5 with 0.5 mL of 0.6 M sodium acetate buffer. The diluted urine was mixed with Glusulase® (9,000 units/mL, 100 µL) and incubated at 37° C. for 1 hr with gentle shaking. The reaction was stopped by the addition of 2 mL of acetone and the precipitate was removed by centrifugation. The supernatant was dried under nitrogen in a TurboVap™ (Caliper Life Sciences, Hopkinton, Mass.). The residues were reconstituted with 1 mL of 60% methanol in water and subsequently analyzed by HPLC and LC/MS, which confirmed the conversion of glucuronide into parent drug tanaproget. Control incubations were conducted under the same conditions, but without adding Glusulase®, or with Glusulase® and 10 mM of saccharolactone (β-glucuronidase inhibitor) and no conversion of glucuronide conjugate into tanaproget was observed.

EXAMPLE 5

Pharmacology

Tanaproget glucuronides are a prodrug of tanaproget, a first-in-class non-steroidal progesterone receptor agonist for use primarily in contraception. The effect of tanaproget glucuronides on alkaline phosphase activity in T47D cells is analyzed as follows.

A. Reagents:

Culture medium: DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM GlutaMax (GIBCO, BRL).

Alkaline phosphatase assay buffer: I. 0.1M Tris-HCl, pH 9.8, containing 0.2% Triton X-100, 0.1M Tris-HCl, pH 9.8, containing 4 mM p-nitrophenyl phosphate (Sigma).

B. Cell Culture And Treatment:

Frozen T47D cells are thawed in a 37° C. water bath and diluted to 280,000 cells/mL in culture medium. To each well in a 96-well plate (Falcon, Becton Dickinson Labware), 180 µl of diluted cell suspension is added.

Twenty µl of reference or test compounds diluted in the culture medium is then added to each well. The cells are incubated at 37° C. in a 5% $CO_2$ humidified atmosphere for 24 hours. For high throughput screening, one concentration of each compound will be tested at 0.3 µg/mL. Based on an average molecular weight of 300 g/mol for the compounds in the library, the concentration is approximately 1 µM.

Subsequently, active compounds will be tested in dose response assays to determine EC50.

C. Alkaline Phosphatase Enzyme Assay:

At the end of treatment, the medium is removed from the plate. Fifty µl of assay buffer I is added to each well. The plates are shaken in a titer plate shaker for 15 min. Then 150 µl of assay buffer II is added to each well. Optical density measurements are taken at 5 min intervals for 30 min at a test wavelength of 405 nM.

D. Analysis of Dose-Response Data.

For reference and test compounds, a dose response curve is generated for dose vs. the rate of enzyme reaction (slope). Square root-transformed data are used for analysis of variance and nonlinear dose response curve fitting for both agonist and antagonist modes. Huber weighting is used to downweight the effects of outliers. $EC_{50}$ values are calculated from the retransformed values. JMP software (SAS Institute, Inc.) is used for both one-way analysis of variance and non-4 linear dose response analysis in both single dose and dose response studies.

E. Results

Tanaproget S-glucuronide had 0.1 nM with 60% efficacy as compared to progesterone.

Tanaproget can be regenerated by enzymatic hydrolysis experiments, such as described in Example 4 above.

EXAMPLE 6

Additional Tanaproget Metabolites

Using the methods described in Example 1 for obtaining the tanaproget glucuronide metabolites, additional tanaproget metabolites were observed in the male rat liver microsomal preparations and in male and female monkey liver microsome preparations using known techniques.

Metabolite M2 was observed in male rat liver microsomal preparations. This metabolite produced a [M−H]-at m/z 312. The product ion at m/z 58 from NCS-, indicating an unchanged thioamide group, was also observed for NSP-989. Product ions at m/z 159 and 195 indicated the pyrrole ring as the site of metabolism. Therefore, metabolite M2 was proposed to be a hydroxy-NSP-989 with the hydroxy group at the pyrrole moiety.

Metabolite M3 was observed in male rat and male and female monkey liver microsome preparations. This metabolite produced a [M−H]-at m/z 312. The product ion at m/z 58 from NCS-, indicating an unchanged thioamide group, was also observed for NSP-989. The product ion at m/z 237, observed for NSP-989 at m/z 220, indicated oxidation of either the phenyl or pyrrole ring. Product ions at m/z 195 and 252 were consistent with oxidation of the phenyl or pyrrole ring. Therefore, metabolite M3 was proposed to be a hydroxy-NSP-989 with the hydroxy group at the phenyl or pyrrole moiety.

Metabolite M4 was observed in all in vitro metabolism samples. This metabolite produced a [M−H]$^-$ at m/z 280, which was 16 atomic mass units (amu) less than NSP-989. The lack of a product ion at m/z 58 and the 16 amu shift in molecular weight indicated a modified thioamide group. Product ions, observed at m/z 129, 220 and 234 were also present for NSP-989. Metabolite M4 also had the same HPLC retention time and product ion spectrum (data not shown) as synthetic NSP-989-carbamate. Therefore, metabolite M4 was identified as NSP-989-carbamate.

Metabolite M6 was observed in dog and in rat liver microsome preparations. This metabolite produced a [M−H]- at m/z 344. The product ions at m/z 80 and 81 indicated the presence of a sulfate group. Product ions at m/z 220 and 234 indicated that the non-thiocarbonyl portions of the NSP-989 molecule were unchanged. Therefore, metabolite M6 was identified as NSP-989 sulfate (6-(5-Cyano-1-methyl-1H-pyrrol-2-yl)-4,4-dimethyl-4H-benzo[d][1,3]oxazine-2-sulfonic acid).

These metabolites can be purified from microsome preparations using methods described above for the glucuronide derivatives. Alternatively, these metabolites can be generated using convention synthetic techniques.

All patent, patent publications, and other publications listed in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A kit for monitoring therapy with tanaproget, said kit comprising a standard comprising a synthetic S-glucuronide of tanaproget of the following structure:

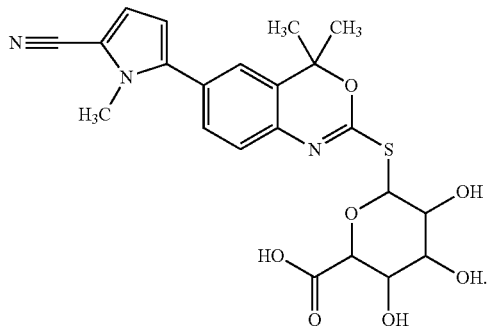 [SMILES: Cn1c(C#N)ccc1-c1ccc2c(c1)C(C)(C)OC(SC1OC(C(=O)O)C(O)C(O)C1O)=N2]

2. A kit for detecting metabolites of tanaproget, said kit comprising packaging and a standard comprising a composition comprising an enzymatically derived tananroget S-glucuronide of the following structure:

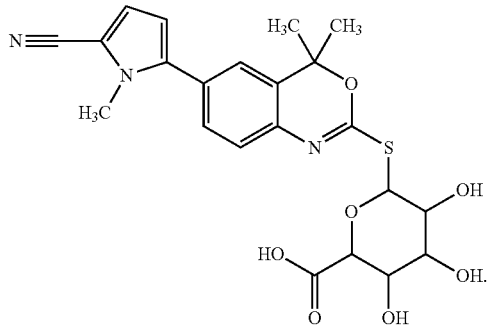 [SMILES: Cn1c(C#N)ccc1-c1ccc2c(c1)C(C)(C)OC(SC1OC(C(=O)O)C(O)C(O)C1O)=N2]

3. A composition comprising a pharmaceutically acceptable carrier and a synthetic N-glucuronide of tanaproget of the following structure:

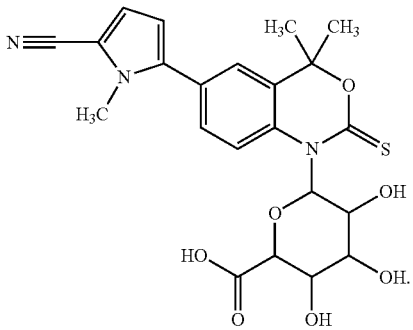 [SMILES: Cn1c(C#N)ccc1-c1ccc2c(c1)C(C)(C)OC(=S)N2C1OC(C(=O)O)C(O)C(O)C1O]

4. A kit for monitoring therapy with tanaproget, said kit comprising a standard comprising a synthetic N-glucuronide of tanaproget of the following structure:

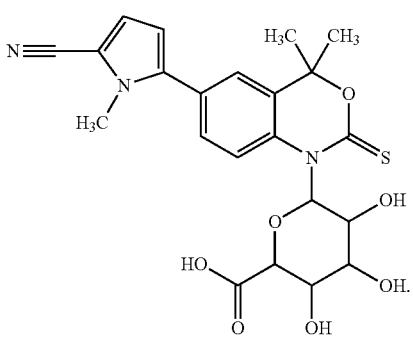 [SMILES: Cn1c(C#N)ccc1-c1ccc2c(c1)C(C)(C)OC(=S)N2C1OC(C(=O)O)C(O)C(O)C1O]

5. A composition useful in an assay for monitoring tanaproget therapy in a subject, said composition comprising a tanaproget metabolite selected from the group consisting of:
   (a) tanaproget having a sulfate moiety located on the thiocarbonyl group;
   (b) tanaproget having a hydroxy group located on the pyrrole ring;
   (c) tanaproget having a hydroxy group located on the phenylpyrrole ring; and
   (d) tanaproget having a carbamate located on the thiocarbonyl group.

6. A kit for detecting metabolites of tanaproget, said kit comprising packaging and a standard comprising a composition according to claim 5.

* * * * *